(12) United States Patent
Rice et al.

(10) Patent No.: US 12,161,530 B2
(45) Date of Patent: *Dec. 10, 2024

(54) WOUND THERAPY SYSTEM WITH WOUND VOLUME ESTIMATION USING GEOMETRIC APPROXIMATION

(71) Applicant: Solventum Intellectual Properties Company, Maplewood, MN (US)

(72) Inventors: Justin R. Rice, San Antonio, TX (US); Christopher A. Carroll, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/203,785

(22) Filed: May 31, 2023

(65) Prior Publication Data
US 2023/0301834 A1 Sep. 28, 2023

Related U.S. Application Data

(63) Continuation of application No. 17/254,393, filed as application No. PCT/US2019/036804 on Jun. 12, 2019, now Pat. No. 11,701,264.
(Continued)

(51) Int. Cl.
*A61F 13/00* (2024.01)
*A61M 1/00* (2006.01)

(52) U.S. Cl.
CPC ......... *A61F 13/00051* (2013.01); *A61M 1/85* (2021.05); *A61M 1/92* (2021.05);
(Continued)

(58) Field of Classification Search
CPC .......... A61M 1/92; A61M 1/85; A61M 1/982; A61M 2205/3379; A61M 2205/3334; A61M 1/777
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Leslie A Lopez
*Assistant Examiner* — Seth Han

(57) ABSTRACT

A wound therapy system includes an instillation fluid canister configured to contain an instillation fluid, a pump fluidly coupled to the instillation fluid canister and operable to deliver the instillation fluid from the instillation fluid canister to a wound, a user interface configured to receive user input indicating one or more geometric attributes of the wound, and a controller electronically coupled to the pump and the user interface. The controller is configured to determine a volume of the wound based on the user input, determine a volume of the instillation fluid to deliver to the wound based on the volume of the wound, and operate the pump to deliver the determined volume of the instillation fluid to the wound.

18 Claims, 14 Drawing Sheets

Related U.S. Application Data

(60) Provisional application No. 62/690,588, filed on Jun. 27, 2018.

(52) U.S. Cl.
CPC ............... *A61M 1/95* (2021.05); *A61M 1/96* (2021.05); *A61M 1/98* (2021.05); *A61M 2205/3379* (2013.01); *A61M 2205/502* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 11,701,264 B2 * | 7/2023 | Rice | A61M 3/022 604/313 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0243073 A1 * | 12/2004 | Lockwood | A61M 1/85 602/41 |
| 2007/0295888 A1 * | 12/2007 | Czarnek | A61B 5/0059 250/206 |
| 2010/0004564 A1 * | 1/2010 | Jendle | A61B 5/107 600/587 |
| 2014/0163491 A1 | 6/2014 | Schuessler et al. | |
| 2015/0080788 A1 | 3/2015 | Blott et al. | |
| 2016/0015872 A1 * | 1/2016 | Luckemeyer | F16K 7/07 604/315 |
| 2018/0050137 A1 * | 2/2018 | Ryu | A61M 1/96 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |

(56) References Cited

FOREIGN PATENT DOCUMENTS

| | | |
|---|---|---|
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

Cuboid

Area

Height (Y)

| | 1 | 2 | 3 | 4 | 5 | 6 | 7 | 8 | 9 | 10 |
|---|---|---|---|---|---|---|---|---|---|---|
| 1 | 1 | 2 | 3 | 4 | 5 | 6 | 7 | 8 | 9 | 10 |
| 2 | 2 | 4 | 6 | 8 | 10 | 12 | 14 | 16 | 18 | 20 |
| 3 | 3 | 6 | 9 | 12 | 15 | 18 | 21 | 24 | 27 | 30 |
| 4 | 4 | 8 | 12 | 16 | 20 | 24 | 28 | 32 | 36 | 40 |
| 5 | 5 | 10 | 15 | 20 | 25 | 30 | 35 | 40 | 45 | 50 |
| 6 | 6 | 12 | 18 | 24 | 30 | 36 | 42 | 48 | 54 | 60 |
| 7 | 7 | 14 | 21 | 28 | 35 | 42 | 49 | 56 | 63 | 70 |
| 8 | 8 | 16 | 24 | 32 | 40 | 48 | 56 | 64 | 72 | 80 |
| 9 | 9 | 18 | 27 | 36 | 45 | 54 | 63 | 72 | 81 | 90 |
| 10 | 10 | 20 | 30 | 40 | 50 | 60 | 70 | 80 | 90 | 100 |

Width (X) — 260

Volume: X × Y × Z

Volume (cuboid)

| 2 | 2 | 4 | 6 | 8 | 10 | 12 | 14 | 16 | 18 | 20 |
|---|---|---|---|---|---|---|---|---|---|---|
| | 4 | 8 | 12 | 16 | 20 | 24 | 28 | 32 | 36 | 40 |
| | 6 | 12 | 18 | 24 | 30 | 36 | 42 | 48 | 54 | 60 |
| | 8 | 16 | 24 | 32 | 40 | 48 | 56 | 64 | 72 | 80 |
| | 10 | 20 | 30 | 40 | 50 | 60 | 70 | 80 | 90 | 100 |
| | 12 | 24 | 36 | 48 | 60 | 72 | 84 | 96 | 108 | 120 |
| | 14 | 28 | 42 | 56 | 70 | 84 | 108 | 112 | 126 | 140 |
| | 16 | 32 | 48 | 64 | 80 | 96 | 112 | 128 | 144 | 160 |
| | 18 | 36 | 54 | 72 | 90 | 108 | 126 | 144 | 162 | 180 |
| | 20 | 40 | 60 | 80 | 100 | 120 | 140 | 160 | 180 | 200 |

| 3 | 3 | 6 | 9 | 12 | 15 | 18 | 21 | 24 | 27 | 30 |
|---|---|---|---|---|---|---|---|---|---|---|
| | 6 | 12 | 18 | 24 | 30 | 36 | 42 | 48 | 56 | 60 |
| | 9 | 6 | 27 | 36 | 45 | 54 | 63 | 72 | 81 | 90 |
| | 12 | 8 | .36 | 48 | 60 | 72 | 84 | 96 | 108 | 120 |
| | 15 | 10 | 45 | 60 | 75 | 90 | 105 | 120 | 135 | 150 |
| | 18 | 12 | 54 | 72 | 90 | 108 | 126 | 144 | 162 | 180 |
| | 21 | 14 | 63 | 84 | 105 | 126 | 147 | 168 | 189 | 210 |
| | 24 | 16 | 72 | 96 | 120 | 144 | 168 | 192 | 216 | 240 |
| | 27 | 18 | 81 | 108 | 135 | 162 | 189 | 216 | 243 | 270 |
| | 30 | 60 | 90 | 120 | 150 | 180 | 210 | 240 | 270 | 300 |

Depth (Z) — 262, 264

Prolate Ellipsoid

Radius A (A=X/2)

280

| Radius B (B=Y/2) | 1 | 2 | 3 | 4 | 5 | 6 | 7 | 8 | 9 | 10 |
|---|---|---|---|---|---|---|---|---|---|---|
| 1 | 1 | 2 | 2 | 3 | 4 | 5 | 5 | 6 | 7 | 8 |
| 2 | 2 | 3 | 5 | 6 | 8 | 9 | 11 | 13 | 14 | 16 |
| 3 | 2 | 5 | 7 | 9 | 12 | 14 | 15 | 19 | 21 | 24 |
| 4 | 3 | 6 | 9 | 13 | 16 | 19 | 22 | 25 | 28 | 31 |
| 5 | 4 | 8 | 12 | 16 | 20 | 24 | 27 | 31 | 35 | 39 |
| 6 | 5 | 9 | 14 | 19 | 24 | 28 | 33 | 38 | 42 | 47 |
| 7 | 5 | 11 | 15 | 22 | 27 | 33 | 38 | 44 | 49 | 55 |
| 8 | 6 | 13 | 19 | 25 | 31 | 38 | 44 | 50 | 57 | 63 |
| 9 | 7 | 14 | 21 | 28 | 35 | 42 | 49 | 57 | 64 | 71 |
| 10 | 8 | 16 | 24 | 31 | 39 | 47 | 55 | 63 | 71 | 79 |

Volume: $\frac{2}{3} \pi \times A \times B \times C$

Volume (half prolate ellipsoid)

Radius C (C=Z) = 2

282

| | 1 | 2 | 3 | 4 | 5 | 6 | 7 | 8 | 9 | 10 |
|---|---|---|---|---|---|---|---|---|---|---|
| 1 | 1 | 2 | 3 | 4 | 5 | 6 | 7 | 8 | 9 | 10 |
| 2 | 2 | 4 | 6 | 8 | 10 | 13 | 15 | 17 | 19 | 21 |
| 3 | 3 | 6 | 9 | 13 | 16 | 19 | 22 | 25 | 28 | 31 |
| 4 | 4 | 8 | 13 | 17 | 21 | 25 | 29 | 34 | 38 | 42 |
| 5 | 5 | 10 | 16 | 21 | 26 | 31 | 37 | 42 | 47 | 52 |
| 6 | 6 | 13 | 19 | 25 | 31 | 38 | 44 | 50 | 57 | 63 |
| 7 | 7 | 15 | 22 | 29 | 37 | 44 | 51 | 59 | 66 | 73 |
| 8 | 8 | 17 | 25 | 34 | 42 | 50 | 59 | 67 | 75 | 84 |
| 9 | 9 | 19 | 28 | 38 | 47 | 57 | 66 | 75 | 85 | 94 |
| 10 | 10 | 21 | 31 | 42 | 52 | 63 | 73 | 84 | 94 | 105 |

Radius C (C=Z) = 3

284

| | 1 | 2 | 3 | 4 | 5 | 6 | 7 | 8 | 9 | 10 |
|---|---|---|---|---|---|---|---|---|---|---|
| 1 | 2 | 3 | 5 | 6 | 8 | 9 | 11 | 13 | 14 | 16 |
| 2 | 3 | 6 | 9 | 13 | 16 | 19 | 22 | 25 | 28 | 31 |
| 3 | 5 | 9 | 14 | 19 | 24 | 28 | 33 | 38 | 42 | 47 |
| 4 | 6 | 13 | 19 | 25 | 31 | 38 | 44 | 50 | 57 | 63 |
| 5 | 8 | 16 | 24 | 31 | 39 | 47 | 55 | 63 | 71 | 79 |
| 6 | 9 | 19 | 28 | 38 | 47 | 57 | 66 | 75 | 85 | 94 |
| 7 | 11 | 22 | 33 | 44 | 55 | 66 | 77 | 88 | 99 | 110 |
| 8 | 13 | 25 | 38 | 50 | 63 | 75 | 88 | 101 | 113 | 126 |
| 9 | 14 | 28 | 42 | 57 | 71 | 85 | 99 | 113 | 127 | 141 |
| 10 | 16 | 31 | 47 | 63 | 79 | 94 | 110 | 126 | 141 | 157 |

WOUND THERAPY SYSTEM WITH WOUND VOLUME ESTIMATION USING GEOMETRIC APPROXIMATION

CROSS-REFERENCE TO RELATED APPLICATIONS

The present application is a continuation of U.S. patent application Ser. No. 17/254,393, entitled "WOUND THERAPY SYSTEM WITH WOUND VOLUME ESTIMATION USING GEOMETRIC APPROXIMATION," filed Dec. 21, 2020, which is a U.S. National Stage Entry of PCT/US2019/036804, entitled "WOUND THERAPY SYSTEM WITH WOUND VOLUME ESTIMATION USING GEOMETRIC APPROXIMATION," filed Jun. 12, 2019, which claims the benefit, under 35 USC § 119(e), of U.S. Provisional Patent Application 62/690,588, entitled "WOUND THERAPY SYSTEM WITH WOUND VOLUME ESTIMATION USING GEOMETRIC APPROXIMATION," filed Jun. 27, 2018, all of which are incorporated herein by reference for all purposes.

BACKGROUND

The present disclosure relates generally to a wound therapy system, and more particularly to a wound therapy system configured to estimate the volume of a wound.

Negative pressure wound therapy (NPWT) is a type of wound therapy that involves applying a negative pressure to a wound site to promote wound healing. Some wound treatment systems apply negative pressure to a wound using a pneumatic pump to generate the negative pressure and flow required. Recent advancements in wound healing with NPWT involve applying topical fluids to wounds to work in combination with NPWT. However, it can be difficult to determine the appropriate volume of instillation fluid to deliver to the wound.

SUMMARY

One implementation of the present disclosure is a wound therapy system. The wound therapy system includes an instillation fluid canister configured to contain an instillation fluid, a pump fluidly coupled to the instillation fluid canister and operable to deliver the instillation fluid from the instillation fluid canister to a wound, a user interface configured to receive user input indicating one or more geometric attributes of the wound, and a controller electronically coupled to the pump and the user interface. The controller is configured to determine a volume of the wound based on the user input, determine a volume of the instillation fluid to deliver to the wound based on the volume of the wound, and operate the pump to deliver the determined volume of the instillation fluid to the wound.

In some embodiments, the one or more geometric attributes of the wound include at least one of a width, a height, or a depth of the wound. The controller can be configured to determine the volume of the wound by applying at least one of the width, the height, or the depth of the wound as an input to a wound volume model.

In some embodiments, the one or more geometric attributes of the wound include a wound shape. The controller can be configured to select a wound volume model based on the wound shape and determine the volume of the wound using the selected wound volume model.

In some embodiments, the one or more geometric attributes of the wound further include at least one of a width, a height, or a depth of the wound. The controller can be configured to determine the volume of the wound by applying at least one of the width, the height, or the depth of the wound as an input to the selected wound volume model.

In some embodiments, the wound volume model defines a relationship between the one or more geometric attributes of the wound and the volume of the wound.

In some embodiments, the wound volume model is a rectangular volume model and the controller is configured to determine the volume of the wound by multiplying the width, the height, and the depth.

In some embodiments, the wound volume model is an elliptical cylinder volume model and the controller is configured to determine the volume of the wound by calculating an ellipse area using the length and the width and multiplying the ellipse area by the depth.

In some embodiments, the wound volume model is a prolate ellipsoid volume model and the controller is configured to determine the volume of the wound based on a volume of a prolate ellipsoid having the length, the width, and the depth. In some embodiments, the controller is configured to determine the volume of the wound by calculating half the volume of the prolate ellipsoid having the length, the width, and the depth.

In some embodiments, the wound therapy system includes a measurement device configured to measure a size of the wound along multiple dimensions of the wound simultaneously. In some embodiments, the measurement device includes a graduated scale printed on packaging of the wound therapy system. In some embodiments, the measurement device includes a transparent sheet having markings indicating length and through which the wound is visible when the measurement device is applied to a surface of the wound.

In some embodiments, the wound therapy system includes one or more tables that define the volume of the wound as a function of the one or more geometric attributes of the wound. In some embodiments, the user input includes the volume of the wound defined by the one or more tables.

In some embodiments, the controller is configured to determine the volume of instillation fluid to deliver to the wound by multiplying the volume of the wound by a fluid instillation factor. In some embodiments, the fluid instillation factor is less than one such that less than a total volume of the wound is filled with the instillation fluid. In some embodiments, the fluid instillation factor is between approximately 0.2 and approximately 0.8.

In some embodiments, the wound therapy system includes a wound dressing sealable to skin surrounding the wound.

In some embodiments, the wound therapy system includes tubing fluidly coupling the pump with the wound. The pump may deliver the determined volume of the instillation fluid to the wound via the tubing.

In some embodiments, the controller is configured to operate the pump to apply negative pressure to the wound.

In some embodiments, the controller is configured to determine the volume of the wound at a plurality of times during wound treatment and determine healing progression based on changes in the volume of the wound during wound treatment.

Another implementation of the present disclosure is a method for delivering instillation fluid to a wound. The method includes receiving user input indicating one or more geometric attributes of the wound at a user interface of a wound therapy device, determining a volume of the wound based on the user input, determining a volume of the instillation fluid to deliver to the wound based on the volume of the wound, and operating a pump of the wound therapy device to deliver the determined volume of the instillation fluid from an instillation fluid canister to the wound.

In some embodiments, the one or more geometric attributes of the wound include at least one of a width, a height, or a depth of the wound. In some embodiments, determining the volume of the wound includes applying at least one of the width, the height, or the depth of the wound as an input to a wound volume model.

In some embodiments, the one or more geometric attributes of the wound include a wound shape. The method may further include selecting a wound volume model based on the wound shape and determining the volume of the wound using the selected wound volume model.

In some embodiments, the one or more geometric attributes of the wound further include at least one of a width, a height, or a depth of the wound. In some embodiments, determining the volume of the wound includes applying at least one of the width, the height, or the depth of the wound as an input to the selected wound volume model.

In some embodiments, the wound volume model defines a relationship between the one or more geometric attributes of the wound and the volume of the wound.

In some embodiments, the wound volume model is a rectangular volume model and determining the volume of the wound includes multiplying the width, the height, and the depth.

In some embodiments, the wound volume model is an elliptical cylinder volume model and determining the volume of the wound includes calculating an ellipse area using the length and the width and multiplying the ellipse area by the depth.

In some embodiments, the wound volume model is a prolate ellipsoid volume model and determining the volume of the wound based on a volume of a prolate ellipsoid having the length, the width, and the depth. In some embodiments, determining the volume of the wound includes calculating half the volume of the prolate ellipsoid having the length, the width, and the depth.

In some embodiments, the method includes using a measurement device to measure a size of the wound along multiple dimensions of the wound simultaneously. In some embodiments, the measurement device includes a graduated scale printed on packaging of the wound therapy system. In some embodiments, the measurement device includes a transparent sheet having markings indicating length and through which the wound is visible when the measurement device is applied to a surface of the wound.

In some embodiments, the method includes using one or more tables to determine the volume of the wound as a function of the one or more geometric attributes of the wound. In some embodiments, the user input includes the volume of the wound defined by the one or more tables.

In some embodiments, determining the volume of instillation fluid to deliver to the wound includes multiplying the volume of the wound by a fluid instillation factor. In some embodiments, the fluid instillation factor is less than one such that less than a total volume of the wound is filled with the instillation fluid. In some embodiments, the fluid instillation factor is between approximately 0.2 and approximately 0.8.

In some embodiments, the method includes sealing a wound dressing to skin surrounding the wound.

In some embodiments, the method includes fluidly coupling the pump with the wound via tubing. In some embodiments, the determined volume of the instillation fluid is delivered to the wound via the tubing.

In some embodiments, the method includes operating the pump to apply negative pressure to the wound.

In some embodiments, the method includes determining the volume of the wound at a plurality of times during wound treatment and determining healing progression based on changes in the volume of the wound during wound treatment.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
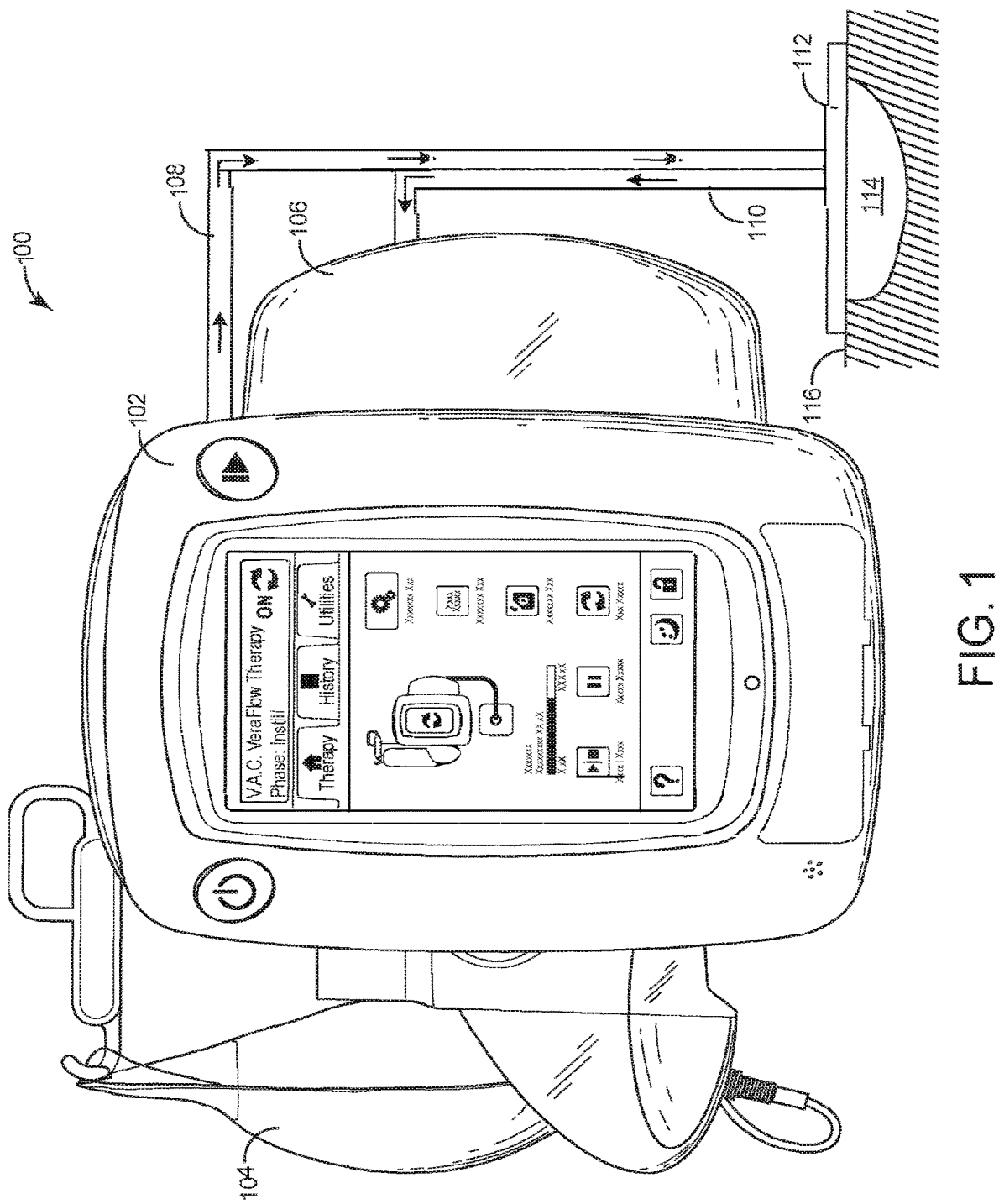
FIG. 1 is a block diagram of a wound therapy system including a therapy device coupled to a wound dressing via tubing, according to an exemplary embodiment.

Referring generally to the FIGURES, a wound therapy system with fluid installation and components thereof are shown, according to various exemplary embodiments. The wound therapy system may include a therapy device and a wound size measurement tool. The therapy device may include an instillation fluid canister, a removed fluid canister, a valve, a pneumatic pump, an instillation pump, and/or a controller. The therapy device can be configured to deliver instillation fluid to the wound and provide negative pressure wound therapy (NPWT) by maintaining the wound at negative pressure.

In some embodiments, the therapy device includes a user interface configured to receive user input indicating one or more geometric attributes of the wound. The geometric attributes can include, for example, a width of the wound, a height or length of the wound, a depth of the wound, a geometric shape of the wound (e.g., rectangular, ellipse cylinder, prolate ellipsoid, triangular, etc.), or other attributes that indicate the size and/or shape of the wound. The controller can use the geometric attributes entered via the user interface to determine a volume of the wound. In other embodiments, the user interface allows a user to enter a volume of the wound directly without specifying geometric attributes. The controller can determine an amount of instillation fluid to deliver to the wound based on the estimated wound volume. These and other features of the wound therapy system are described in detail below.

Wound Therapy System

Referring now to FIGS. 1-4, a negative pressure wound therapy (NPWT) system 100 is shown, according to an exemplary embodiment. NPWT system 100 is shown to include a therapy device 102 fluidly connected to a wound dressing 112 via tubing 108 and 110. Wound dressing 112 may be adhered or sealed to a patient's skin 116 surrounding a wound 114. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, U.S. patent application Ser. No. 14/087,418 filed Nov. 22, 2013, and U.S. Provisional Patent Application No. 62/650,132 filed Mar. 29, 2018. The entire disclosure of each of these patents and patent applications is incorporated by reference herein.

Therapy device 102 can be configured to provide negative pressure wound therapy by reducing the pressure at wound 114. Therapy device 102 can draw a vacuum at wound 114 (relative to atmospheric pressure) by removing wound exudate, air, and other fluids from wound 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound 114 may include instillation fluid 105 previously delivered to wound 114. Instillation fluid 105 can include, for example, a cleansing fluid, a prescribed fluid, a medicated fluid, an antibiotic fluid, or any other type of fluid which can be delivered to wound 114 during wound treatment. Instillation fluid 105 may be held in an instillation fluid canister 104 and controllably dispensed to wound 114 via instillation fluid tubing 108. In some embodiments, instillation fluid canister 104 is detachable from therapy device 102 to allow canister 106 to be refilled and replaced as needed.

Fluids 107 removed from wound 114 pass through removed fluid tubing 110 and are collected in removed fluid canister 106. Removed fluid canister 106 may be a component of therapy device 102 configured to collect wound exudate and other fluids 107 removed from wound 114. In some embodiments, removed fluid canister 106 is detachable from therapy device 102 to allow canister 106 to be emptied and replaced as needed. A lower portion of canister 106 may be filled with wound exudate and other fluids 107 removed from wound 114, whereas an upper portion of canister 106 may be filled with air. Therapy device 102 can be configured to draw a vacuum within canister 106 by pumping air out of canister 106. The reduced pressure within canister 106 can be translated to wound dressing 112 and wound 114 via tubing 110 such that wound dressing 112 and wound 114 are maintained at the same pressure as canister 106.

Figure 2:
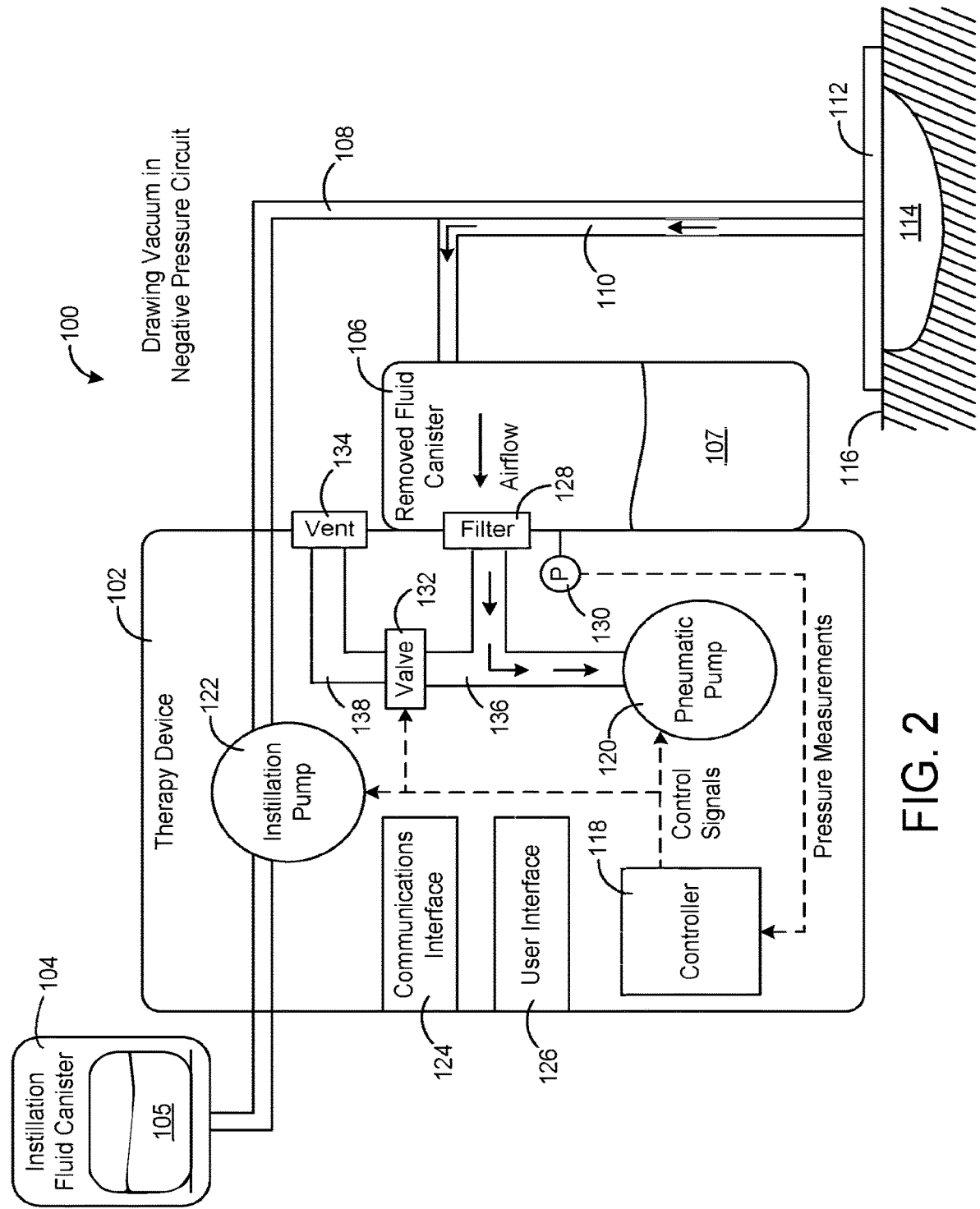
FIG. 2 is a block diagram illustrating the therapy device of FIG. 1 in greater detail when the therapy device operates to draw a vacuum within a negative pressure circuit, according to an exemplary embodiment.
Figure 3:
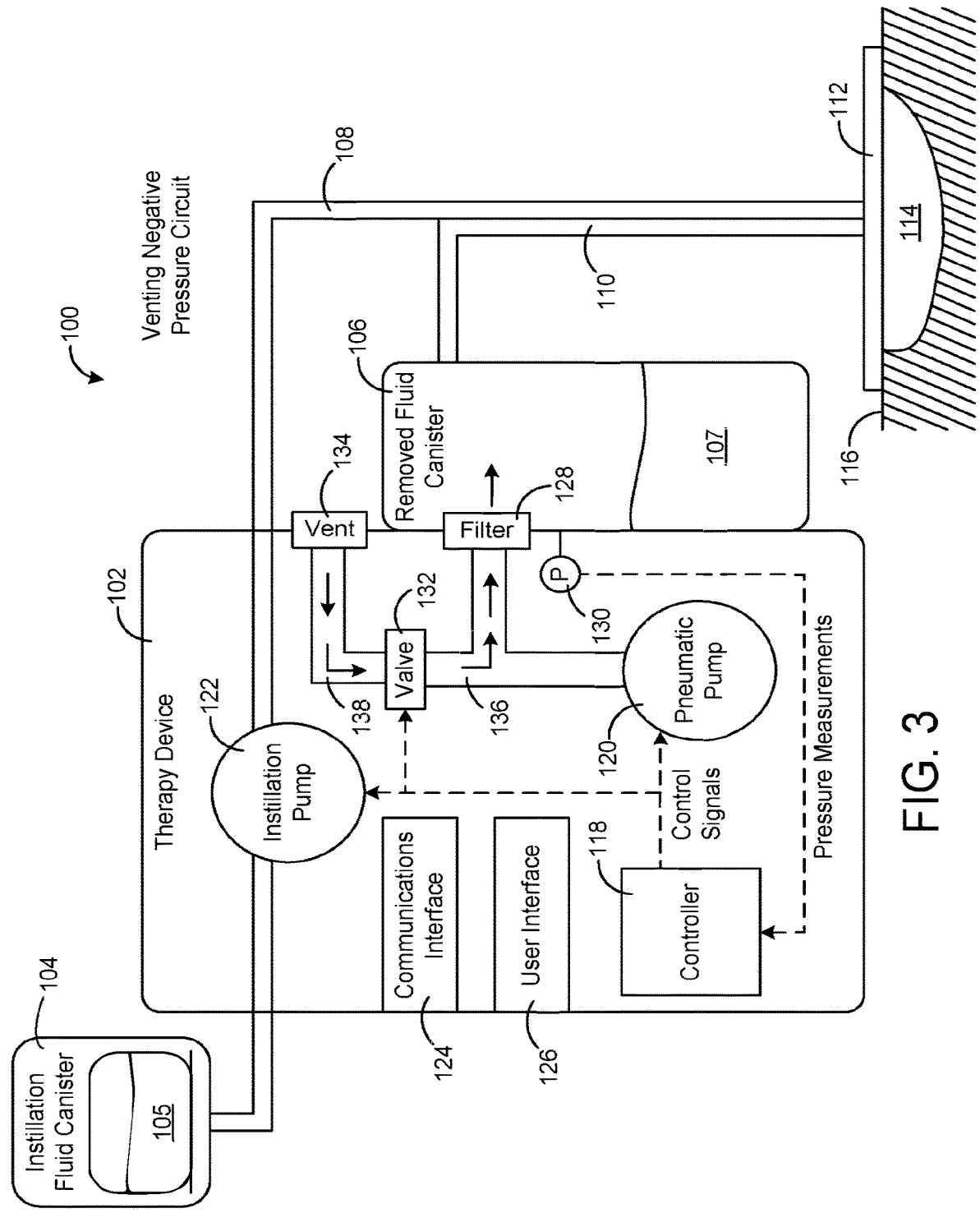
FIG. 3 is a block diagram illustrating the therapy device of FIG. 1 in greater detail when the therapy device operates to vent the negative pressure circuit, according to an exemplary embodiment.
Figure 4:
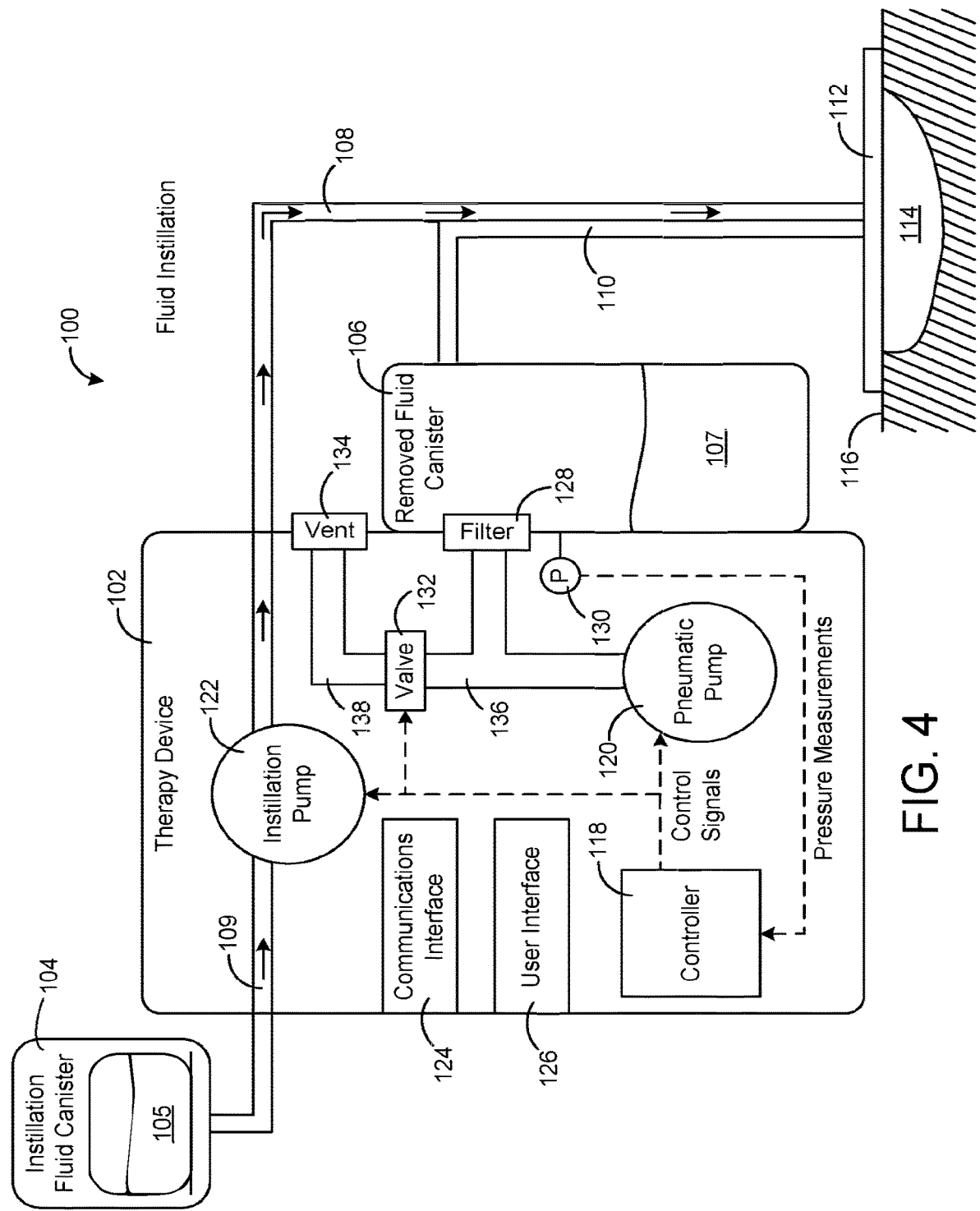
FIG. 4 is a block diagram illustrating the therapy device of FIG. 1 in greater detail when the therapy device operates to deliver instillation fluid to the wound dressing and/or a wound, according to an exemplary embodiment.

Referring particularly to FIGS. 2-4, block diagrams illustrating therapy device 102 in greater detail are shown, according to an exemplary embodiment. Therapy device 102 is shown to include a pneumatic pump 120, an instillation pump 122, a valve 132, a filter 128, and a controller 118. Pneumatic pump 120 can be fluidly coupled to removed fluid canister 106 (e.g., via conduit 136) and can be configured to draw a vacuum within canister 106 by pumping air out of canister 106. In some embodiments, pneumatic pump 120 is configured to operate in both a forward direction and a reverse direction. For example, pneumatic pump 120 can operate in the forward direction to pump air out of canister 106 and decrease the pressure within canister 106. Pneumatic pump 120 can operate in the reverse direction to pump air into canister 106 and increase the pressure within canister 106. Pneumatic pump 120 can be controlled by controller 118, described in greater detail below.

Similarly, instillation pump 122 can be fluidly coupled to instillation fluid canister 104 via tubing 109 and fluidly coupled to wound dressing 112 via tubing 108. Instillation pump 122 can be operated to deliver instillation fluid 105 to wound dressing 112 and wound 114 by pumping instillation fluid 105 through tubing 109 and tubing 108, as shown in FIG. 4. Instillation pump 122 can be controlled by controller 118, described in greater detail below.

Filter 128 can be positioned between removed fluid canister 106 and pneumatic pump 120 (e.g., along conduit 136) such that the air pumped out of canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound 114 from therapy device 102).

Valve 132 can be fluidly connected with pneumatic pump 120 and filter 128 via conduit 136. In some embodiments, valve 132 is configured to control airflow between conduit 136 and the environment around therapy device 102. For example, valve 132 can be opened to allow airflow into conduit 136 via vent 134 and conduit 138, and closed to prevent airflow into conduit 136 via vent 134 and conduit 138. Valve 132 can be opened and closed by controller 118. When valve 132 is closed, pneumatic pump 120 can draw a vacuum within a negative pressure circuit by causing airflow through filter 128 in a first direction, as shown in FIG. 2. The negative pressure circuit may include any component of system 100 that can be maintained at a negative pressure when performing negative pressure wound therapy (e.g., conduit 136, removed fluid canister 106, tubing 110, wound dressing 112, and/or wound 114). For example, the negative pressure circuit may include conduit 136, removed fluid canister 106, tubing 110, wound dressing 112, and/or wound 114. When valve 132 is open, airflow from the environment around therapy device 102 may enter conduit 136 via vent 134 and conduit 138 and fill the vacuum within the negative pressure circuit. The airflow from conduit 136 into canister 106 and other volumes within the negative pressure circuit may pass through filter 128 in a second direction, opposite the first direction, as shown in FIG. 3.

In some embodiments, therapy device 102 includes a variety of sensors. For example, therapy device 102 is shown to include a pressure sensor 130 configured to measure the pressure within canister 106 and/or the pressure at wound dressing 112 or wound 114. Pressure measurements recorded by pressure sensor 130 can be communicated to controller 118. Controller 118 use the pressure measurements to ensure that wound 114 is maintained at negative pressure. For example, controller 118 can activate pneumatic pump 120 in response to the pressure measurement from pressure sensor 130 exceeding a negative pressure setpoint in order to reduce the pressure at wound 114.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. In some embodiments, the pressure measurements recorded by pressure sensor 130 are presented to a user via user interface 126. User interface 126 can also display alerts generated by controller 118. For example, controller 118 can generate a "no canister" alert if canister 106 is not detected and present the no canister alert via user interface 126.

In some embodiments, user interface 126 is configured to receive user input indicating one or more geometric attributes of wound 114. The geometric attributes can include, for example, a width of wound 114, a height or length of wound 114, a depth of wound 114, a geometric shape of wound 114 (e.g., rectangular, ellipse cylinder, prolate ellipsoid, triangular, etc.), or other attributes that indicate the size and/or shape of wound 114. Controller 118 can use the geometric attributes entered via user interface 126 to determine a volume of wound 114 and determine an amount of instillation fluid 105 to deliver to wound 114 based on the estimated wound volume. In other embodiments, user interface 126 allows a user to enter a volume of wound 114 directly without specifying geometric attributes.

Figure 6:
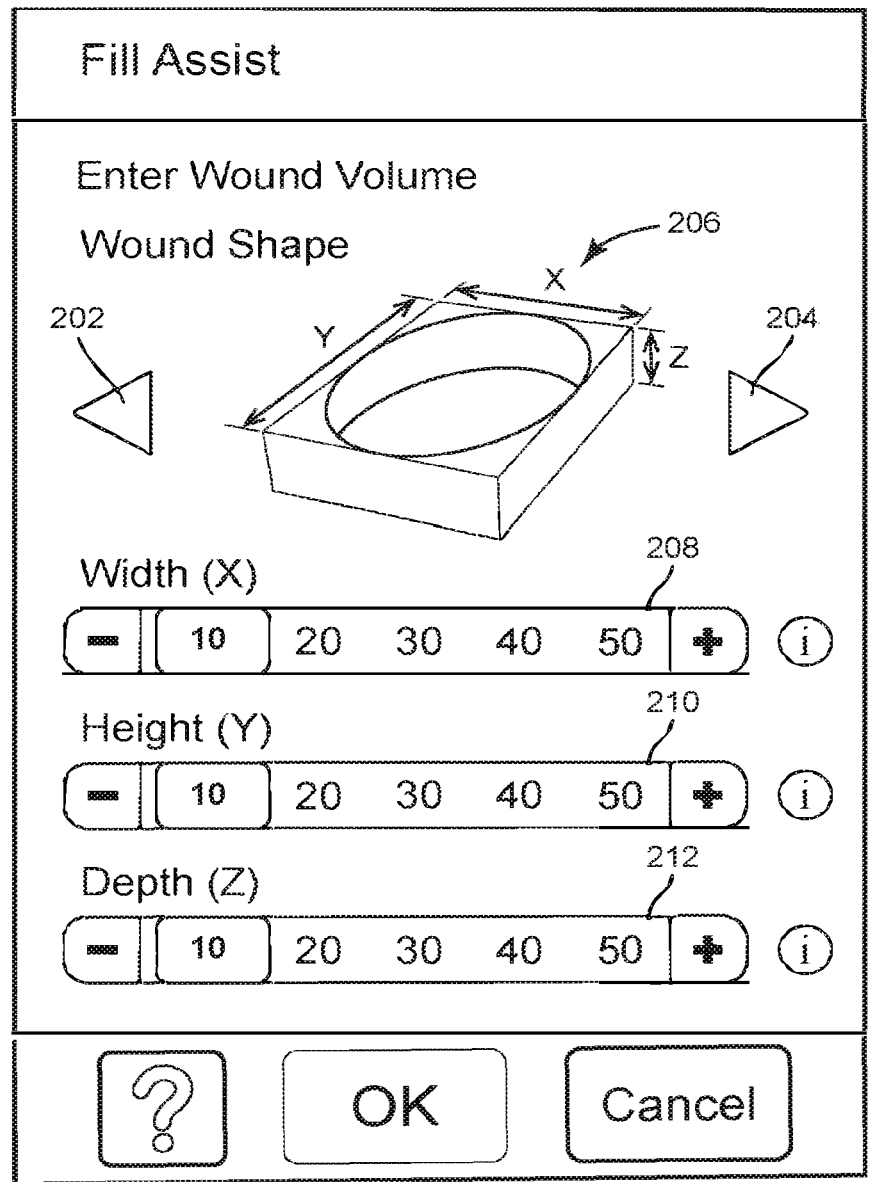
FIG. 6 is a fill assist interface which can be generated by the therapy device of FIG. 1, according to an exemplary embodiment.

Referring now to FIG. 6, a fill assist interface 200 which can be presented via user interface 126 is shown, according to an exemplary embodiment. Fill assist interface 200 may prompt a user to select a wound shape 206 and may include an illustration of the selected wound shape 206. Selecting either of arrows 202 and 204 may cause fill assist interface 200 to cycle through a set of wound shapes 206 which can be selected (e.g., rectangular, ellipse cylinder, prolate ellipsoid, triangular prism, etc.). In FIG. 6, fill assist interface 200 is shown displaying an ellipse cylinder wound shape 206 having a width x, a height y, and a depth z. However, wound shape 206 may switch to other wound shapes in response to a user selecting either of arrows 202 and 204. Several other wound shapes 206 which can be selected and displayed via fill assist interface 200 are shown in FIGS. 7A-7D.

Fill assist interface 200 is shown to include geometric attribute selectors 208, 210, and 212. Each of geometric attribute selectors 208-212 may correspond to a particular dimension of the selected wound shape 206 and may allow a user to specify the size of wound 114 along that dimension. For example, selector 208 corresponds to the width dimension x and allows a user to specify the width x of wound 114. Similarly, selector 210 corresponds to the height dimension y and allows a user to specify the height y of wound 114, whereas selector 212 corresponds to the depth dimension z and allows a user to specify the depth z of wound 114. The user can select from any of the preset values shown in fill assist interface 200 (e.g., 10 mm, 20 mm, 30 mm, etc.) or enter a custom value not shown in fill assist interface 200 (e.g., 27 mm, 31 mm, etc.).

Referring again to FIGS. 1-4, in some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

Controller 118 can be configured to operate pneumatic pump 120, instillation pump 122, valve 132, and/or other controllable components of therapy device 102. In some embodiments, controller 118 automatically determines the volume of wound 114 based on user input received via user interface 126. For example, controller 118 can determine the volume of wound 114 by applying the geometric attributes of wound 114 (e.g., wound shape, height, width, depth, etc.) as an input to a wound volume model. In some embodiments, controller 118 uses the specified wound shape to select an appropriate wound volume model. For example, controller 118 can select a rectangular wound volume model in response to a user selecting a rectangular wound shape via user interface 126, a prolate ellipsoid wound volume model in response to a user selecting a prolate ellipsoid wound shape via user interface 126, or any other type of geometric model in response to a user selecting the corresponding wound shape via user interface 126.

In some embodiments, controller 118 applies the specified height, width, depth, or other geometric attributes of wound 114 as inputs to the selected wound volume model to calculate the volume of wound 114. For example, the rectangular wound volume model may define the volume of wound 114 as a product of the width x, height y, and depth z of wound 114 (i.e., $V_{wound}=xyz$), whereas the prolate ellipsoid wound volume model may define the volume of wound 114 as $$V_{wound} = \frac{2}{3}\pi abc$$

(i.e., halt the volume of a prolate ellipsoid), where a is the radius of wound 114 along the width dimension (i.e., a=x/2), b is the radius of wound 114 along the height dimension (i.e., b=y/2), and c is the radius of wound 114 along the depth dimension (i.e., c=z). In other embodiments, controller 118 determines the volume of wound 114 directly from the user input. For example, a user can specify the volume of wound 114 via user interface 126 such that controller 118 can determine the volume of wound 114 without performing any calculations.

Controller 118 can determine a volume of instillation fluid 105 to deliver to wound 114 based on the volume of wound 114. In some embodiments, controller 118 determines the volume $V_{fluid}$ of instillation fluid 105 to deliver to wound 114 by multiplying the volume $V_{wound}$ of wound 114 by a fluid instillation factor α (i.e., $V_{fluid}=aV_{wound}$). The fluid instillation factor α may be less than one such that less than the total volume $V_{wound}$ of wound 114 is filled with instillation fluid 105. In some embodiments, the fluid instillation factor α is between approximately 0.2 and approximately 0.8. Controller 118 can then operate instillation pump 122 to deliver the determined volume $V_{fluid}$ of instillation fluid 105 to wound 114. These and other features of controller 118 are described in greater detail below.

Controller

Figure 5:
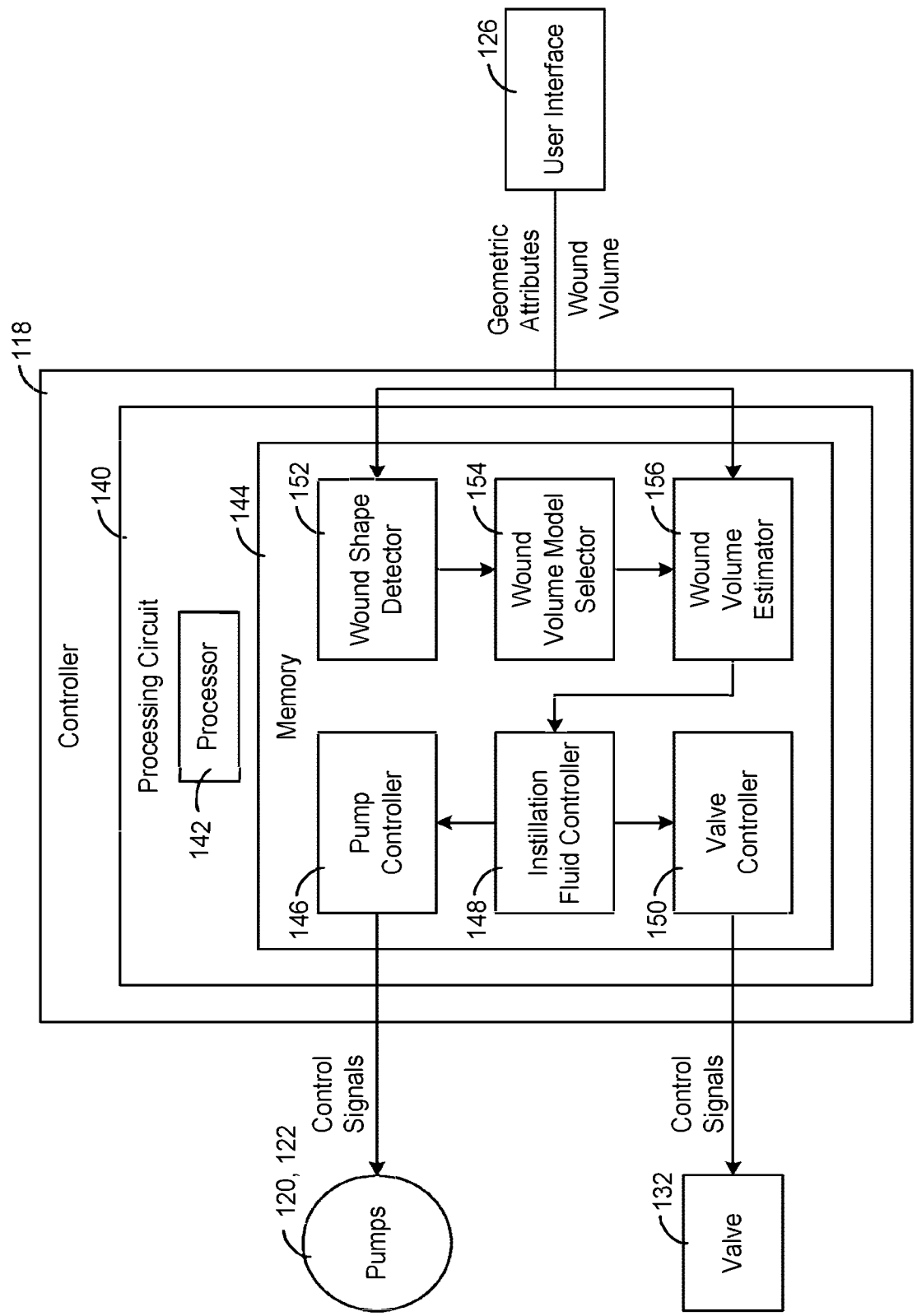
FIG. 5 is a block diagram illustrating a controller of the therapy device of FIG. 1 in greater detail, according to an exemplary embodiment.

Referring now to FIG. 5, a block diagram illustrating controller 118 in greater detail is shown, according to an exemplary embodiment. Controller 118 is shown to include a processing circuit 140 including a processor 142 and memory 144. Processor 142 may be a general purpose or specific purpose processor, an application specific integrated circuit (ASIC), one or more field programmable gate arrays (FPGAs), a group of processing components, or other suitable processing components. Processor 142 is configured to execute computer code or instructions stored in memory 144 or received from other computer readable media (e.g., CDROM, network storage, a remote server, etc.).

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions. Memory 144 may include database components, object code components, script components, or any other type of information structure for supporting the various activities and information structures described in the present disclosure. Memory 144 may be communicably connected to processor 142 via processing circuit 140 and may include computer code for executing (e.g., by processor 142) one or more processes described herein. When processor 142 executes instructions stored in memory 144, processor 142 generally configures controller 118 (and more particularly processing circuit 140) to complete such activities.

Controller 118 is shown to include a pump controller 146 and a valve controller 150. Pump controller 146 can be configured to operate pumps 120 and 122 by generating and providing control signals to pumps 120-122. The control signals provided to pumps 120-122 can cause pumps 120-122 to activate, deactivate, or achieve a variable capacity or speed (e.g., operate at half speed, operate at full speed, etc.). Similarly, valve controller 150 can be configured to operate valve 132 by generating and providing control signals to valve 132. The control signals provided to valve 132 can cause valve 132 to open, close, or achieve a specified intermediate position (e.g., one-third open, half open, etc.). In some embodiments, pump controller 146 and valve controller 150 are used by other components of controller 118 (e.g., instillation fluid controller 148, wound volume estimator 156, etc.) to operate pumps 120-122 and valve 132 when carrying out the processes described herein.

In some embodiments, pump controller 146 uses input from a canister sensor configured to detect whether removed fluid canister 106 is present. Pump controller 146 can be configured to activate pneumatic pump 120 only when removed fluid canister 106 is present. For example, pump controller 146 can check whether canister 106 is present and can activate pneumatic pump 120 in response to a determination that canister 106 is present. However, if canister 106 is not present, pump controller 146 may prevent pneumatic pump 120 from activating. Similarly, pump controller 146 can be configured to activate instillation pump 122 only when instillation fluid canister 104 is present. For example, pump controller 146 can check whether canister 104 is present and can activate instillation pump 122 in response to a determination that canister 104 is present. However, if canister 104 is not present, pump controller 146 may prevent instillation pump 122 from activating.

Figure 7A:
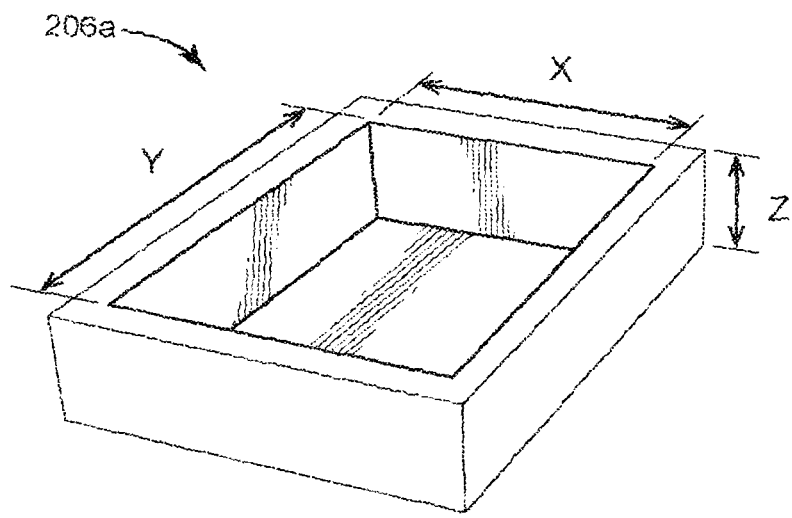
FIG. 7A is an illustration of a rectangular wound shape which can be selected via the fill assist interface of FIG. 6, according to an exemplary embodiment.
Figure 7B:
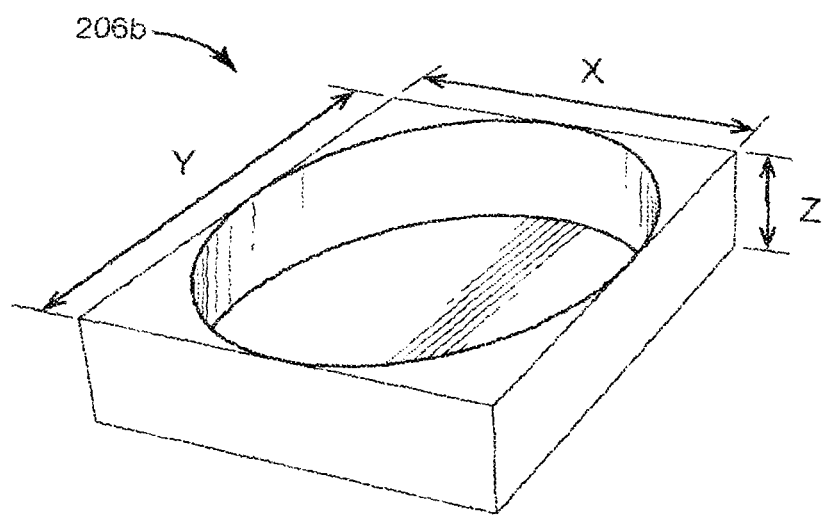
FIG. 7B is an illustration of an ellipse cylinder wound shape which can be selected via the fill assist interface of FIG. 6, according to an exemplary embodiment.

Controller 118 is shown to include a wound shape detector 152 and a wound volume model selector 154. Wound shape detector 152 can be configured to identify the wound shape specified via user interface 126. A user can select any of a variety of wound shapes that most closely matches the shape of wound 114. Examples of wound shapes that can be selected via user interface 126 may include a rectangular wound shape, an elliptical cylinder wound shape, a prolate ellipsoid wound shape, a triangular prism wound shape, or any other wound shape. Several examples of wound shapes 206a-206d which can be selected via user interface 126 and detected by wound shape detector 152 are shown in FIGS. 7A-7B. Wound shape detector 152 can provide an indication of the selected wound shape to wound volume model selector 154.

Wound volume model selector 154 can be configured to select a wound volume model corresponding to the wound shape detected by wound shape detector 152. Wound volume model selector 154 may store a variety of different wound volume models, each of which corresponds to a different wound shape. Each wound volume model may be a geometric model that defines the volume $V_{wound}$ of wound 114 as a function of the geometric attributes received via user interface 126 (e.g., the width x, height y, and depth z of wound 114). The function that relates the volume $V_{wound}$ of wound 114 to the geometric attributes x, y, and z may vary based on the selected wound shape.

Referring now to FIG. 7A, a rectangular wound shape 206a is shown, according to an exemplary embodiment. Rectangular wound shape 206a is shown to include a width x, a height y, and a depth z. Wound volume model selector 154 may select a rectangular wound volume model in response to wound shape detector 152 detecting rectangular wound shape 206a. The rectangular wound volume model may define the volume $V_{wound}$ of wound 114 as a product of the width x, height y, and depth z as shown in the following equation:

$$V_{wound}=xYz$$

where x is the width of wound 114, y is the height of wound 114, and z is the depth of wound 114.

Referring now to FIG. 7B, an ellipse cylinder wound shape 206b is shown, according to an exemplary embodiment. Ellipse cylinder wound shape 206b is shown to include a width x, a height y, and a depth z. Wound volume model selector 154 may select an ellipse cylinder wound volume model in response to wound shape detector 152 detecting ellipse cylinder shape 206b. The ellipse cylinder wound volume model may define the volume $V_{wound}$ of wound 114 as a function of axial radii a and b and cylinder depth c, as shown in the following equation:

$$V_{wound}=\pi abc$$

where a is the axial radius of wound 114 along the width dimension x (i.e., a=x/2), b is the axial radius of wound 114 along the height dimension y (i.e., b=y/2), and c is the depth of wound 114 along the depth dimension z (i.e., c=z).

Figure 7C:
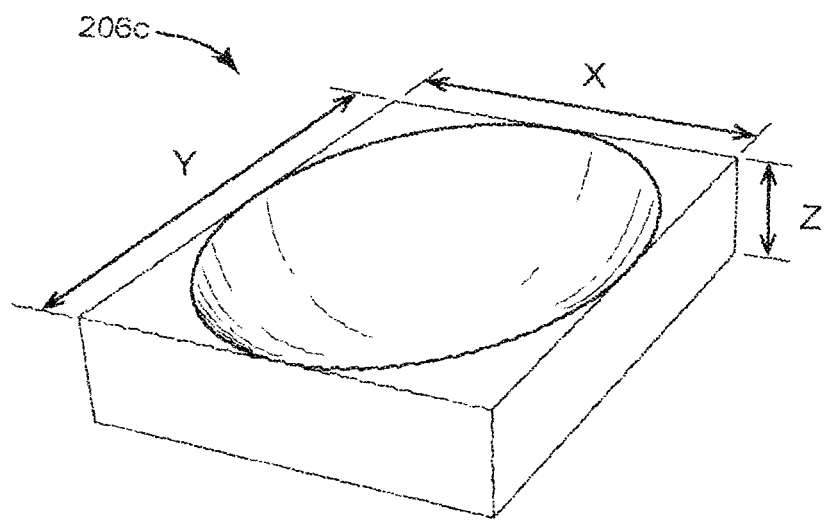
FIG. 7C is an illustration of a prolate ellipsoid wound shape which can be selected via the fill assist interface of FIG. 6, according to an exemplary embodiment.

Referring now to FIG. 7C, a prolate ellipsoid wound shape 206c is shown, according to an exemplary embodiment. Prolate ellipsoid wound shape 206c is shown to include a width x, a height y, and a depth z. Wound volume model selector 154 may select a prolate ellipsoid wound volume model in response to wound shape detector 152 detecting prolate ellipsoid wound shape 206c. The prolate ellipsoid wound volume model may define the volume $V_{wound}$ of wound 114 as a function of axial radii a, b, and c, as shown in the following equation:

$$V_{wound} = \frac{2}{3}\pi abc$$

where a is the axial radius of wound 114 along the width dimension (i.e., a=x/2), b is the axial radius of wound 114 along the height dimension (i.e., b=y/2), and c is the axial radius of wound 114 along the depth dimension (i.e., c=z). The volume $V_{wound}$ of prolate ellipsoid wound shape 206c can be defined as half the volume of a prolate ellipsoid having axial radii a, b, and c.

Figure 7D:
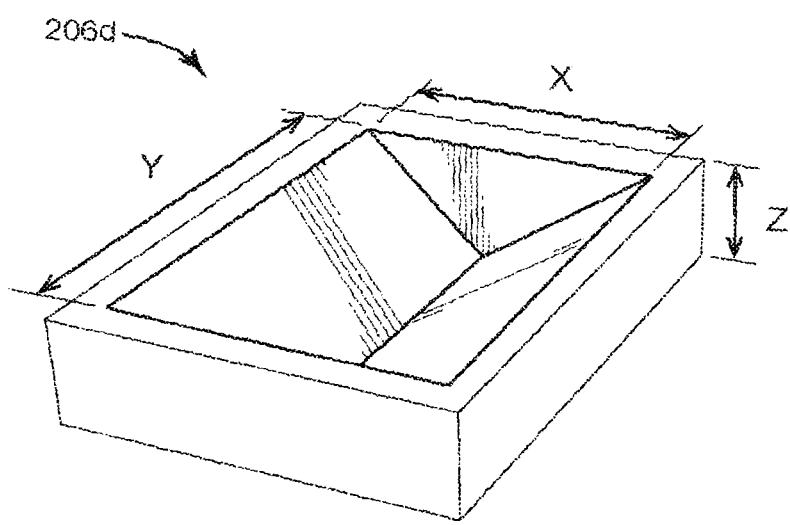
FIG. 7D is an illustration of a triangular wound shape which can be selected via the fill assist interface of FIG. 6, according to an exemplary embodiment.

Referring now to FIG. 7D, a triangular wound shape 206d is shown, according to an exemplary embodiment. Triangular wound shape 206d is shown to include a width x, a height y, and a depth z. Wound volume model selector 154 may select a triangular wound volume model in response to wound shape detector 152 detecting triangular wound shape 206d. The triangular wound volume model may define the volume $V_{wound}$ of wound 114 as a function of the width x, height y, and depth z as shown in the following equation:

$$V_{wound} = \frac{xyz}{2}$$

where x is the width of a triangular face of wound 114, y is the height of wound 114, and z is the depth of a triangular face of wound 114.

Referring again to FIG. 5, controller 118 is shown to include a wound volume estimator 156 and a fluid instillation controller 148. Wound volume estimator 156 may receive the selected wound volume model from wound volume selector 154 and may receive the geometric attributes of wound 114 (e.g., width x, height y, and depth z) from user interface 126. Wound volume estimator 156 may apply the geometric attributes as inputs to the selected wound volume model to calculate the volume $V_{wound}$ of wound 114. In some embodiments, wound volume estimator 156 calculates the variables a, b, and c based on the values of x, y, and z for use in the ellipse cylinder wound volume model and the prolate ellipsoid wound volume model, as shown in the following equations:

$$a = \frac{x}{2}$$
$$b = \frac{y}{2}$$
$$c = z$$

In some embodiments, the user input received via user interface 126 includes the wound volume $V_{wound}$. In this scenario, wound volume estimator 156 can estimate the volume $V_{wound}$ of wound 114 directly from the user input (i.e., by simply identifying the user-specified wound volume) without performing any calculations. Wound volume estimator 156 may provide the estimated wound volume $V_{wound}$ to instillation fluid controller 148.

Instillation fluid controller 148 can determine a volume of instillation fluid 105 to deliver to wound 114 based on the volume $V_{wound}$ of wound 114. In some embodiments, instillation fluid controller 148 determines the volume $V_{fluid}$ of instillation fluid 105 to deliver to wound 114 by multiplying the volume $V_{wound}$ of wound 114 by a fluid instillation factor α, as shown in the following equation:

$$V_{fluid}=aV_{wound}$$

In some embodiments, the fluid instillation factor α is less than one such that less than the total volume $V_{wound}$ of wound 114 is filled with instillation fluid 105. For example, the fluid instillation factor α may be between approximately 0.2 and approximately 0.8. Instillation fluid controller 148 can then operate instillation pump 122 to deliver the determined volume $V_{fluid}$ of instillation fluid 105 to wound 114 (e.g., by providing control signals to pump controller 146).

Measurement Tool

Figure 8:
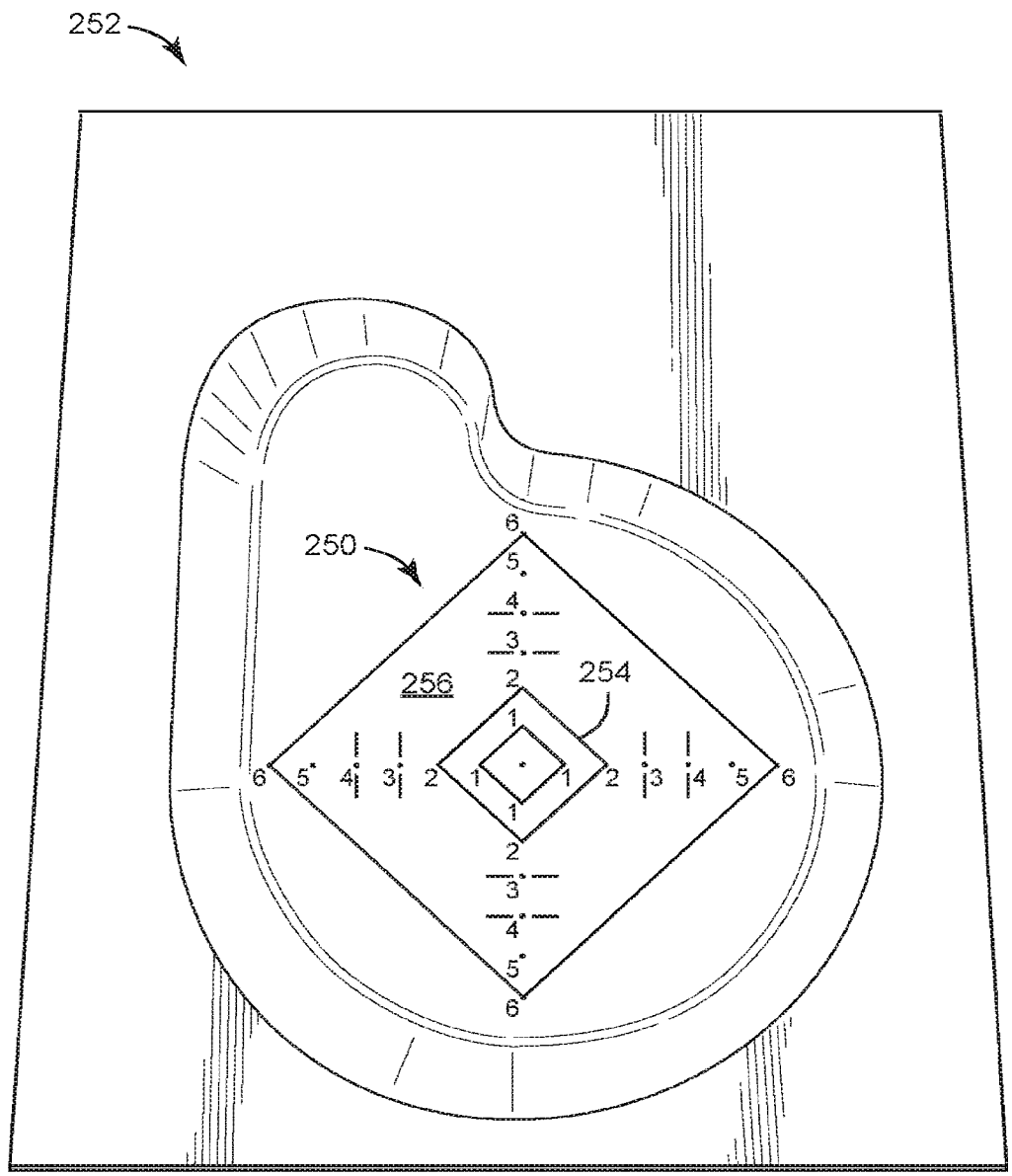
FIG. 8 is a drawing of a measurement tool which can be part of the wound therapy system of FIG. 1, according to an exemplary embodiment.
Figure 9:
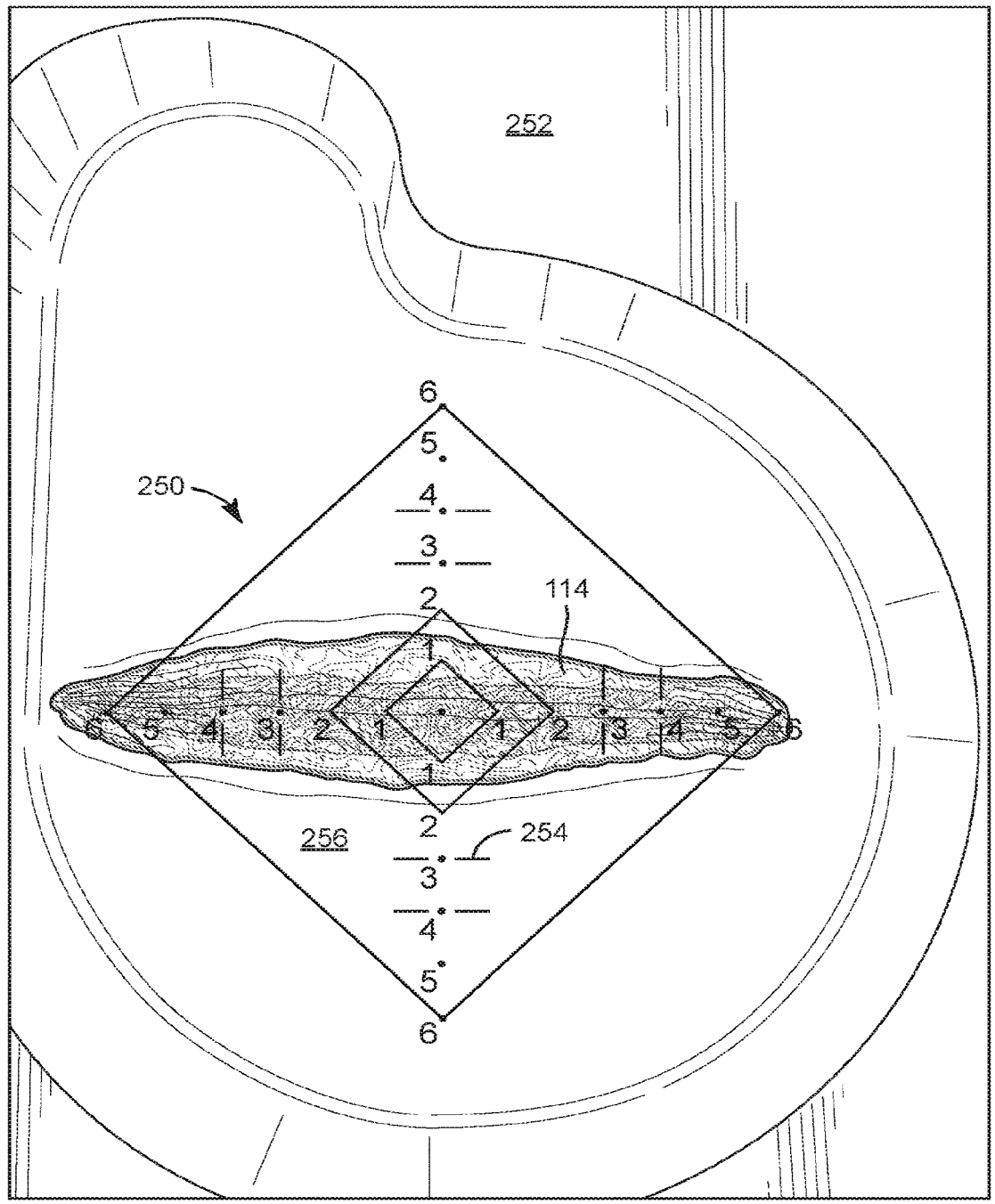
FIG. 9 is a drawing of the measurement tool of FIG. 8 overlaid onto a wound during wound size measurement, according to an exemplary embodiment.

Referring now to FIGS. 8-9, a measurement tool 250 is shown, according to an exemplary embodiment. Measurement tool 250 may be part of wound therapy system 100 and can be used to measure the width x, height y, depth z, and/or other geometric attributes of wound 114. The measurements provided by measurement tool 250 can be provided as an input to fill assist interface 200. In some embodiments, measurement tool 250 is configured to measure a size of wound 114 along multiple dimensions of wound 114 simultaneously. For example, measurement tool 250 is shown to include a two-dimensional graduated scale 254 that can be used to simultaneously measure the width x and height y of wound 114.

In some embodiments, measurement tool 250 includes a transparent sheet 256 having markings (i.e., graduated scale 254) indicating the size of wound 114 along multiple dimensions. As shown in FIG. 9, wound 114 may be visible through transparent sheet 256 when measurement tool 250 is applied to a surface of wound 114 and/or overlaid with wound 114. In some embodiments, graduated scale 254 is printed on transparent or semi-transparent packaging 252 of wound therapy system 100. In other embodiments, graduated scale 254 and transparent sheet 256 may be included as a separate component of wound therapy system 100 (i.e., a separate transparent sheet) within packaging 252.

REFERENCE TABLES

Figure 10:
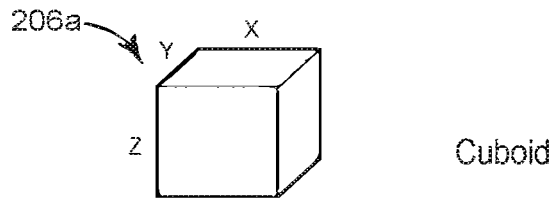
FIG. 10 is a set of rectangular reference tables for estimating the volume of a wound having a rectangular wound shape, according to an exemplary embodiment.
Figure 11:
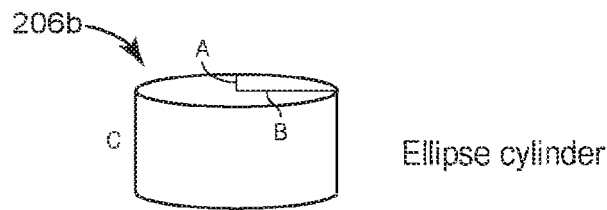
FIG. 11 is a set of ellipse cylinder reference tables for estimating the volume of a wound having an ellipse cylinder wound shape, according to an exemplary embodiment.
Figure 12:
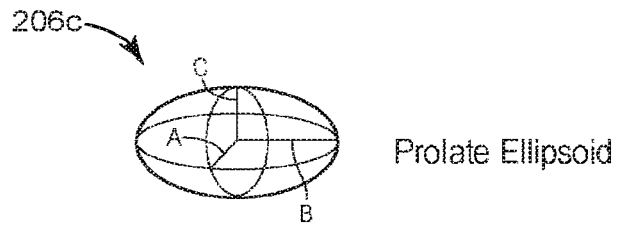
FIG. 12 is a set of prolate ellipsoid reference tables for estimating the volume of a wound having a prolate ellipsoid wound shape, according to an exemplary embodiment.

Referring now to FIGS. 10-12, several reference tables 260-284 are shown, according to an exemplary embodiment. Reference tables 260-284 may define the volume $V_{Wound}$ of wound 114 as a function of the width x, height y, depth z, and/or other geometric attributes of wound 114. Reference tables 260-284 can be used as an alternative to the automatic wound volume calculations performed by wound volume estimator 156. In some embodiments, reference tables 260-284 are part of wound therapy system 100 and may be included within the packaging of wound therapy system 100.

Referring particularly to FIG. 10, a set of rectangular reference tables 260, 262, and 264 are shown. Rectangular reference tables 260-264 can be used to estimate the volume of wound 114 when wound 114 has a rectangular wound shape 206a. Area table 260 defines the area $A_{wound}$ of wound 114 as a function of the width x and the height y. Volume tables 262 and 264 define the volume $V_{Wound}$ of wound 114 as a function of the area $A_{wound}$ specified by area table 260 and the depth z of wound 114. For example, a given wound 114 may rectangular-shaped have a width of 5 cm, a height of 6 cm, and a depth of 2 cm. Area table 260 defines the area $A_{wound}$ of such a wound as 30 cm². Volume table 262 is specific to a wounds having a depth of 2 cm, whereas volume table 264 is specific to wounds having a depth of 3 cm. Because the wound has a volume of 2 cm, volume table 262 can be used to find the volume $V_{Wound}$ corresponding to the area of 30 cm², which is shown in volume table 262 as 60 cm³.

Referring now to FIG. 11, a set of ellipse cylinder reference tables 270, 272, and 274 are shown. Ellipse cylinder reference tables 270-274 can be used to estimate the volume of wound 114 when wound 114 has an ellipse cylinder wound shape 206b. Area table 270 defines the area $A_{wound}$ of wound 114 as a function of the width x and the height y. Volume tables 272 and 274 define the volume $V_{Wound}$ of wound 114 as a function of the area $A_{wound}$ specified by area table 270 and the depth z of wound 114. For example, a given ellipse cylinder-shaped wound 114 may have a width of 3 cm, a height of 7 cm, and a depth of 2 cm. Area table 270 defines the area $A_{wound}$ of such a wound as 16 cm². Volume table 272 is specific to a wounds having a depth of 2 cm, whereas volume table 274 is specific to wounds having a depth of 3 cm. Because the wound has a volume of 2 cm, volume table 272 can be used to find the volume $V_{wound}$ corresponding to the area of 16 cm², which is shown in volume table 272 as 33 cm³.

Referring now to FIG. 12, a set of prolate ellipsoid reference tables 280, 282, and 284 are shown. Prolate ellipsoid reference tables 280-284 can be used to estimate the volume of wound 114 when wound 114 has a prolate ellipsoid wound shape 206c. Area table 280 defines the area $A_{wound}$ of wound 114 as a function of the width x and the height y. Volume tables 282 and 284 define the volume $V_{Wound}$ of wound 114 as a function of the area $A_{wound}$ specified by area table 280 and the depth z of wound 114. For example, a given prolate ellipsoid-shaped wound 114 may have a width of 4 cm, a height of 9 cm, and a depth of 3 cm. Area table 280 defines the area $A_{wound}$ of such a wound as 28 cm². Volume table 282 is specific to a wounds having a depth of 2 cm, whereas volume table 284 is specific to wounds having a depth of 3 cm. Because the wound has a volume of 3 cm, volume table 284 can be used to find the volume $V_{wound}$ corresponding to the area of 28 cm², which is shown in volume table 284 as 38 cm³. Notably, the volumes defined by volume tables 282-284 are half the volumes of a prolate ellipsoid having the specified width x, height y, depth z because wound 114 is only the bottom half of the prolate ellipsoid.

Flow Diagrams

Figure 13:
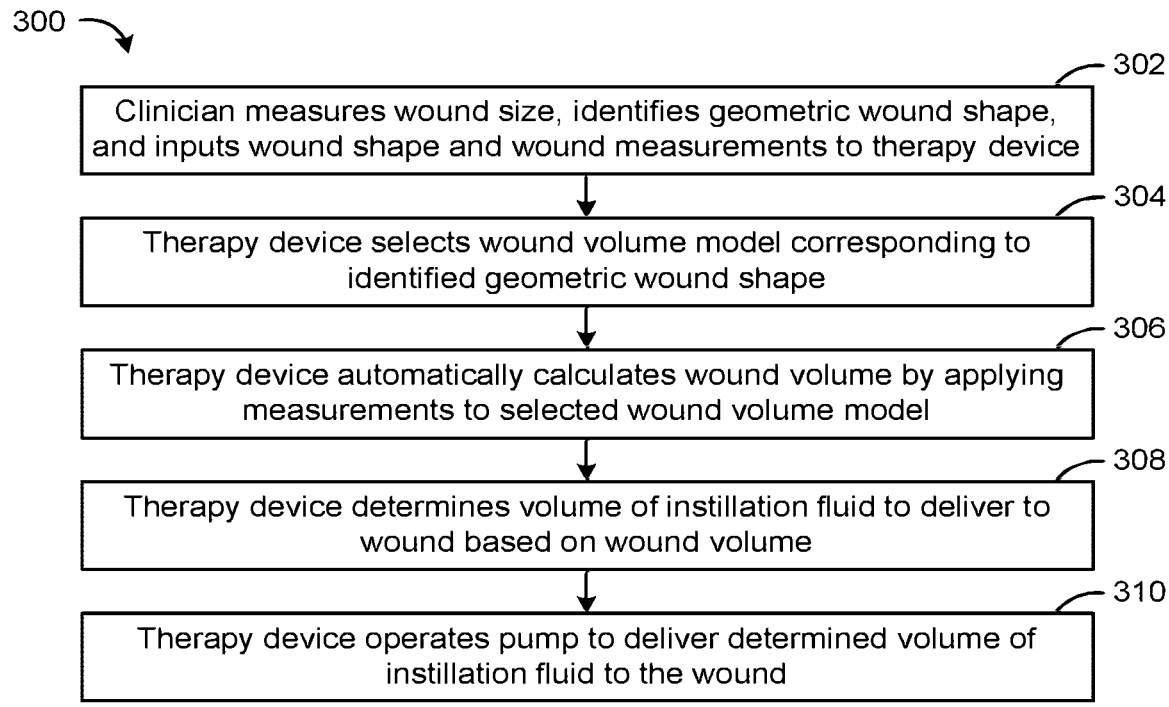
FIG. 13 is a flowchart of a process for automatically estimating a wound volume based on geometric attributes of the wound and delivering instillation fluid to the wound based on the estimated wound volume, according to an exemplary embodiment.

Referring now to FIG. 13, a flowchart of a process 300 for delivering instillation fluid to a wound is shown, according to an exemplary embodiment. Process 300 can be performed by one or more components of therapy device 102. For example, process 300 can be performed by controller 118, user interface 126, pneumatic pump 120, and/or other components of therapy device 102.

Process 300 is shown to include measuring a wound size, identifying a geometric wound shape, and inputting the wound shape and wound size measurements into therapy device 102 (step 302). In some embodiments, step 302 is performed by a clinician using measurement tool 250. For example, the clinician can use measurement tool 250 to measure the width and height of wound 114. A separate ruler can be used to measure the depth of wound 114. The clinician can determine whether the geometric shape of wound 114 is most similar to rectangular wound shape 206a, ellipse cylinder wound shape 206b, prolate ellipsoid wound shape 206c, triangular wound shape 206d, or any other wound shape that has a corresponding wound volume model within therapy device 102. The wound measurements and the wound shape can be input to therapy device 102 via user interface 126.

Process 300 is shown to include selecting a wound volume model corresponding to the identified geometric wound shape (step 304). In some embodiments, step 304 is performed by wound volume model selector 154. Wound volume model selector 154 may store a variety of different wound volume models, each of which corresponds to a different wound shape. Each wound volume model may be a geometric model that defines the volume $V_{wound}$ of wound 114 as a function of the geometric attributes received via user interface 126 (e.g., the width x, height y, and depth z of wound 114). The function that relates the volume $V_{wound}$ of wound 114 to the geometric attributes x, y, and z may vary based on the selected wound shape. Several examples of wound volume models and corresponding geometric wound shapes 206a-206d are described in detail with reference to FIGS. 7A-7D.

Process 300 is shown to include automatically calculating the wound volume $V_{wound}$ by applying the measurements of wound 114 to the selected wound volume model (step 306). If the selected wound volume model is a rectangular wound volume model, step 306 may include calculating the volume $V_{wound}$ of wound 114 as a product of the width x, height y, and depth z as shown in the following equation:

$$V_{wound} = xyz$$

where x is the width of wound 114, y is the height of wound 114, and z is the depth of wound 114.

If the selected wound volume model is an ellipse cylinder wound volume model, step 306 may include calculating the volume $V_{wound}$ of wound 114 as a function of axial radii a and b and cylinder depth c, as shown in the following equation:

$$V_{wound} = \pi abc$$

where a is the axial radius of wound 114 along the width dimension x (i.e., a=x/2), b is the axial radius of wound 114 along the height dimension y (i.e., b=y/2), and c is the depth of wound 114 along the depth dimension z (i.e., c=z).

If the selected wound volume model is a prolate ellipsoid wound volume model, step 306 may include calculating the volume $V_{wound}$ of wound 114 as a function of axial radii a, b, and c, as shown in the following equation:

$$V_{wound} = \frac{2}{3}\pi abc$$

where a is the axial radius of wound 114 along the width dimension (i.e., a=x/2), b is the axial radius of wound 114 along the height dimension (i.e., b=y/2), and c is the axial radius of wound 114 along the depth dimension (i.e., c=z). The volume $V_{wound}$ of prolate ellipsoid wound shape 206c can be defined as half the volume of a prolate ellipsoid having axial radii a, b, and c.

If the selected wound volume model is a triangular wound volume model, step 306 may include calculating the volume $V_{wound}$ of wound 114 as a function of the width x, height y, and depth z as shown in the following equation:

$$V_{wound} = \frac{xyz}{2}$$

where x is the width of a triangular face of wound 114, y is the height of wound 114, and z is the depth of a triangular face of wound 114.

In some embodiments, step 306 includes calculating the variables a, b, and c based on the values of x, y, and z for use in the ellipse cylinder wound volume model and the prolate ellipsoid wound volume model, as shown in the following equations:

$$a = \frac{x}{2}$$
$$b = \frac{y}{2}$$
$$c = z$$

Process 300 is shown to include determining a volume $V_{fluid}$ of instillation fluid 105 to deliver to wound 114 based on the volume $V_{wound}$ of wound 114 (step 308) and operating a pump to deliver the determined volume $V_{fluid}$ of instillation fluid 105 to wound 114 (step 310). In some embodiments, step 308 includes determining the volume $V_{fluid}$ of instillation fluid 105 to deliver to wound 114 by multiplying the volume $V_{wound}$ of wound 114 by a fluid instillation factor α, as shown in the following equation:

$$V_{fluid} = aV_{wound}$$

In some embodiments, the fluid instillation factor α is less than one such that less than the total volume $V_{wound}$ of wound 114 is filled with instillation fluid 105. For example, the fluid instillation factor α may be between approximately 0.2 and approximately 0.8. Step 310 may include operating instillation pump 122 to deliver the determined volume $V_{fluid}$ of instillation fluid 105 to wound 114 (e.g., by providing control signals to pump controller 146).

Figure 14:
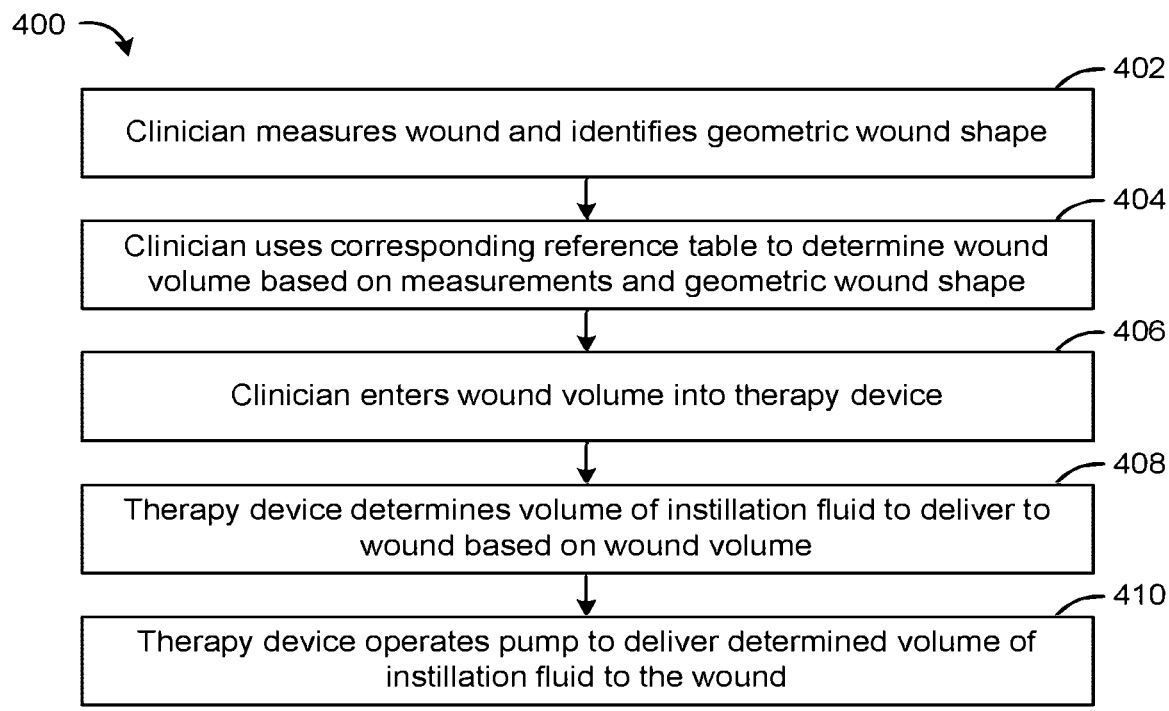
FIG. 14 is a flowchart of a process for estimating a wound volume using reference tables and delivering instillation fluid to the wound based on the estimated wound volume, according to an exemplary embodiment.

Referring now to FIG. 14, a flowchart of another process 400 for delivering instillation fluid to a wound is shown, according to an exemplary embodiment. Process 400 can be performed by one or more components of therapy device 102. For example, process 300 can be performed by controller 118, user interface 126, pneumatic pump 120, and/or other components of therapy device 102.

Process 400 is shown to include measuring a wound size and identifying a geometric wound shape (step 402). In some embodiments, step 402 is performed by a clinician using measurement tool 250. For example, the clinician can use measurement tool 250 to measure the width and height of wound 114. A separate ruler can be used to measure the depth of wound 114. The clinician can determine whether the geometric shape of wound 114 is most similar to rectangular wound shape 206a, ellipse cylinder wound shape 206b, prolate ellipsoid wound shape 206c, triangular wound shape 206d, or any other wound shape that has a corresponding reference table for estimating the wound volume.

Process 400 is shown to include using a corresponding reference table to determine the wound volume $V_{wound}$ based on the wound size measurements and the geometric wound shape (step 404). Each geometric wound shape may have a corresponding reference table or set of reference tables. For example, reference tables 260-264 can be used to determine the wound volume $V_{wound}$ for wounds having a rectangular wound shape 206a. Reference tables 270-274 can be used to determine the wound volume $V_{wound}$ for wounds having an ellipse cylinder wound shape 206b. Reference tables 280-284 can be used to determine the wound volume $V_{wound}$ for wounds having a prolate ellipsoid wound shape 206c. The wound volume $V_{wound}$ specified by the reference tables can then be input to therapy device 102 via user interface 126 (step 406).

Process 400 is shown to include determining a volume $V_{fluid}$ of instillation fluid 105 to deliver to wound 114 based on the volume $V_{wound}$ of wound 114 (step 408) and operating a pump to deliver the determined volume $V_{fluid}$ of instillation fluid 105 to wound 114 (step 410). In some embodiments, step 408 includes determining the volume $V_{fluid}$ of instillation fluid 105 to deliver to wound 114 by multiplying the volume $V_{wound}$ of wound 114 by a fluid instillation factor α, as shown in the following equation:

$$V_{fluid} = aV_{wound}$$

In some embodiments, the fluid instillation factor α is less than one such that less than the total volume $V_{wound}$ of wound 114 is filled with instillation fluid 105. For example, the fluid instillation factor α may be between approximately 0.2 and approximately 0.8. Step 410 may include operating instillation pump 122 to deliver the determined volume $V_{fluid}$ of instillation fluid 105 to wound 114 (e.g., by providing control signals to pump controller 146).

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

The invention claimed is:

1. A therapy device comprising:
    a user interface configured to receive user input indicating at least one geometric attribute of a wound; and
    a controller electronically coupled to the user interface, the controller configured to:
        in response to the at least one geometric attribute of the wound, determine a volume of the wound;
        in response to the determined volume of the wound, determine a volume of instillation fluid to deliver to the wound; and
        actuate delivery of the determined volume of the instillation fluid to the wound.

2. The therapy device of claim 1, wherein the controller further comprises a processing circuit comprising:
    a processor; and
    memory communicably connected to the processor;
    a wound shape detector configured to receive the at least one geometric attribute of the wound and identify a wound shape;
    a wound volume model selector configured to select a wound volume model in response to the wound shape identified by the wound shape detector;
    a wound volume estimator configured to receive the at least one geometric attribute and the wound volume model and in response determines the volume of the wound;
    an instillation fluid controller configured to receive the volume of the wound and, in response, determine the volume of the instillation fluid to deliver to the wound;
    a valve controller configured to generate one or more control signals to be received by one or more valves; and
    a pump controller configured to generate one or more control signals to be received by one or more pumps.

3. The therapy device of claim 2, further comprising:
    a canister sensor configured to detect a presence of a removed fluid canister, the canister sensor communicably coupled to the pump controller; and
    the pump controller further configured to generate the one or more control signals in response to a signal from the canister sensor.

4. The therapy device of claim 2, further comprising:
    a canister sensor configured to detect a presence of a instillation fluid canister, the canister sensor communicably coupled to the pump controller; and
    the pump controller further configured to generate the one or more control signals in response to a signal from the canister sensor.

5. The therapy device of claim 2, further comprising:
    an instillation pump communicably coupled to the pump controller and configured to deliver instillation fluid in response to the one or more control signals from the pump controller; and
    a pneumatic pump communicably coupled to the pump controller and configured to generate a negative pressure in response to the one or more control signals from the pump controller.

6. The therapy device of claim 2, further comprising a valve communicably coupled to the valve controller and configured to actuate in response to the one or more control signals from the valve controller.

7. The therapy device of claim 1, wherein:
    the at least one geometric attribute of the wound comprise at least one of a width, a height, or a depth of the wound; and
    the controller is configured to determine the volume of the wound by applying at least one of the width, the height, or the depth of the wound as an input to a wound volume model.

8. The therapy device of claim 1, wherein:
    the at least one geometric attribute of the wound comprise a wound shape; and the controller is configured to:
        select a wound volume model based on the wound shape; and
        determine the volume of the wound using the selected wound volume model.

9. The therapy device of claim 8, wherein:
    the at least one geometric attribute of the wound further comprise at least one of a width, a height, or a depth of the wound; and
    the controller is configured to determine the volume of the wound by applying at least one of the width, the height, or the depth of the wound as an input to the selected wound volume model.

10. A kit for providing wound therapy, the kit comprising:
    a therapy device comprising:
        a user interface configured to receive user input indicating at least one geometric attribute of a wound; and
        a controller electronically coupled to the user interface, the controller configured to:
            in response to the at least one geometric attribute of the wound, determine a volume of the wound;

in response to the determined volume of the wound, determine a volume of instillation fluid to deliver to the wound; and actuate delivery of the determined volume of the instillation fluid to the wound; and a wound measurement tool for estimating a wound volume, the measurement tool comprising a transparent sheet having markings indicating a size of a wound along multiple dimensions.

11. The kit claim 10, wherein the controller further comprises a processing circuit comprising:

a processor; and memory communicably connected to the processor;

a wound shape detector configured to receive the at least one geometric attribute of the wound and identify a wound shape;

a wound volume model selector configured to select a wound volume model in response to the wound shape identified by the wound shape detector;

a wound volume estimator configured to receive the at least one geometric attribute and the wound volume model and in response determines the volume of the wound;

an instillation fluid controller configured to receive the volume of the wound and, in response, determine the volume of the instillation fluid to deliver to the wound;

a valve controller configured to generate one or more control signals to be received by one or more valves; and a pump controller configured to generate one or more control signals to be received by one or more pumps.

12. The kit of claim 11, further comprising:

a canister sensor configured to detect a presence of a removed fluid canister, the canister sensor communicably coupled to the pump controller; and the pump controller further configured to generate the one or more control signals in response to a signal from the canister sensor.

13. The kit of claim 11, further comprising:

a canister sensor configured to detect a presence of a instillation fluid canister, the canister sensor communicably coupled to the pump controller; and the pump controller further configured to generate the one or more control signals in response to a signal from the canister sensor.

14. The kit of claim 11, further comprising:

an instillation pump communicably coupled to the pump controller and configured to deliver instillation fluid in response to the one or more control signals from the pump controller; and a pneumatic pump communicably coupled to the pump controller and configured to generate a negative pressure in response to the one or more control signals from the pump controller.

15. The kit of claim 11, further comprising a valve communicably coupled to the valve controller and configured to actuate in response to the one or more control signals from the valve controller.

16. The kit of claim 10, wherein:

the at least one geometric attribute of the wound comprise at least one of a width, a height, or a depth of the wound; and the controller is configured to determine the volume of the wound by applying at least one of the width, the height, or the depth of the wound as an input to a wound volume model.

17. The kit of claim 10, wherein:

the at least one geometric attribute of the wound comprise a wound shape; and the controller is configured to:

select a wound volume model based on the wound shape; and determine the volume of the wound using the selected wound volume model.

18. The kit of claim 17 wherein:

the at least one geometric attribute of the wound further comprise at least one of a width, a height, or a depth of the wound; and the controller is configured to determine the volume of the wound by applying at least one of the width, the height, or the depth of the wound as an input to the selected wound volume model.

* * * * *